(12) United States Patent
Engh et al.

(10) Patent No.: US 8,808,386 B2
(45) Date of Patent: *Aug. 19, 2014

(54) MODULAR APPARATUS AND METHOD FOR SCULPTING THE SURFACE OF A JOINT

(75) Inventors: Gerard A. Engh, Alexandria, VA (US); Wesley D. Johnson, Eden Prairie, MN (US)

(73) Assignee: Cayenne Medical, Inc., Scottsdale, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 12/818,962

(22) Filed: Jun. 18, 2010

(65) Prior Publication Data

US 2011/0015749 A1   Jan. 20, 2011

Related U.S. Application Data

(60) Division of application No. 11/186,485, filed on Jul. 20, 2005, now Pat. No. 7,758,652, and a continuation-in-part of application No. 10/159,147, filed on May 29, 2002, now Pat. No. 7,115,131, which is a division of application No. 09/882,591, filed on Jun. 14, 2001, now Pat. No. 6,482,209.

(60) Provisional application No. 60/589,320, filed on Jul. 20, 2004.

(51) Int. Cl.
*A61F 2/38* (2006.01)

(52) U.S. Cl.
USPC .................................................. 623/20.15

(58) Field of Classification Search
CPC ..... A61F 2/30724; A61F 2/38; A61F 2/4684; A61F 2310/00952; A61F 2/30942; A61F 2/34; A61F 2/3662; A61F 2/3859; A61F 2/3872; A61F 2/3877; A61F 2/389; A61F 2/30767; A61F 2002/30092; A61F 2002/30616; A61F 2002/30884; A61F 2002/30894; A61F 2002/30668; A61F 2002/3895; A61F 2002/4623; A61F 2002/4631; A61F 2002/4635; A61F 2002/4681; A61F 2002/4693
USPC ............ 623/20.21, 20.35, 20.15, 20.3, 20.33, 623/20.34, 20.36, 20.28, 20.14, 20.18, 623/23.41, 23.27, 23.44, 20.32, 20.24
See application file for complete search history.

(56) References Cited

U.S. PATENT DOCUMENTS

| 5,011,497 | A | 4/1991 | Persson et al. |
| 6,749,638 | B1 * | 6/2004 | Saladino ............ 623/20.14 |

(Continued)

FOREIGN PATENT DOCUMENTS

| CA | 2640576 A1 | 12/2004 | |
| GB | 2312168 | * 10/1997 | ............ 623/20.21 |

(Continued)

OTHER PUBLICATIONS

European Search Report, Issued by the European Patent Office regarding corresponding patent application Serial No. EP 05773733.0, mailed Jan. 7, 2013; 12 pages.

(Continued)

*Primary Examiner* — Pedro Philogene
(74) *Attorney, Agent, or Firm* — Barbara A. Wrigley; Oppenheimer Wolff & Donnelly LLP

(57) ABSTRACT

The present invention provides a modular device for restoring individual joint kinematics using minimally invasive surgical procedures. The modular implants include distinct components that include tethering means. The modular implants provide intraoperative surgical options for articular constraint and facilitate proper alignment and orientation of the joint to restore kinematics as defined by the individual patient anatomy.

34 Claims, 12 Drawing Sheets

(56) References Cited

U.S. PATENT DOCUMENTS

| | | |
|---|---|---|
| 6,802,867 B2 | 10/2004 | Manasas et al. |
| 7,615,081 B2 * | 11/2009 | Justin et al. ............... 623/20.14 |
| 7,758,652 B2 * | 7/2010 | Engh et al. ................. 623/20.21 |
| 7,799,084 B2 * | 9/2010 | Clemow et al. ............ 623/20.15 |
| 8,048,163 B2 * | 11/2011 | Coon et al. ................. 623/20.15 |
| 2002/0055783 A1 * | 5/2002 | Tallarida et al. ........... 623/20.14 |
| 2002/0138150 A1 | 9/2002 | Leclercq |
| 2002/0198528 A1 | 12/2002 | Engh et al. |
| 2003/0050645 A1 | 3/2003 | Parker et al. |
| 2003/0158606 A1 | 8/2003 | Coon et al. |
| 2003/0225457 A1 | 12/2003 | Justin et al. |
| 2004/0015174 A1 | 1/2004 | Null et al. |
| 2004/0102852 A1 | 5/2004 | Johnson et al. |
| 2004/0138683 A1 | 7/2004 | Shelton et al. |
| 2006/0004460 A1 | 1/2006 | Engh et al. |
| 2006/0009853 A1 | 1/2006 | Justin et al. |
| 2006/0058884 A1 | 3/2006 | Aram et al. |
| 2006/0155380 A1 | 7/2006 | Clemnow et al. |

FOREIGN PATENT DOCUMENTS

| | | |
|---|---|---|
| GB | 2312168 A | 10/1997 |
| JP | 2002291779 | 10/2002 |

OTHER PUBLICATIONS

Office Action, issued by the Canadian Patent Office, regarding corresponding patent application Serial No. 2574290, dated Jan. 2, 2014, 2 pages.

Examination Report, issued by the Indian Intellectual Property Office, regarding corresponding patent application Serial No. 223/DELNP/2007, dated Dec. 13, 2013, 2 pages.

* cited by examiner

MODULAR APPARATUS AND METHOD FOR SCULPTING THE SURFACE OF A JOINT

CROSS REFERENCE TO RELATED APPLICATIONS

This application is a divisional of U.S. patent application Ser. No. 11/186,485, filed Jul. 20, 2005, which claims priority to U.S. provisional patent application Ser. No. 60/589,320 filed Jul. 20, 2004, and which is a continuation-in-part of U.S. patent application Ser. No. 10/159,147 filed May 29, 2002, now U.S. Pat. No. 7,115,131, which is a divisional of U.S. patent application Ser. No. 09/882,591 filed Jun. 14, 2001, now U.S. Pat. No. 6,482,209, the entireties of which are hereby incorporated by reference.

BACKGROUND OF THE INVENTION

1. Field of the Invention

This invention relates to implants for use in minimally invasive total knee replacement surgery. More particularly, this invention relates to modular bearing surfaces and mobile-bearing and fixed-bearing modular components in arthroplasty of human joints.

2. Description of the Related Art

A joint, such as the ankle, knee, hip or shoulder, generally consists of two or more relatively rigid bony structures that maintain a relationship with each other. Soft tissue structures spanning the bony structures hold the bony structures together and aid in defining the motion of one bony structure to the other. In the knee, for example, the bony structures are the femur, tibia and patella. Soft tissue structures spanning the knee joint, such as muscles, ligaments, tendons, menisci, and capsule, provide force, support and stability to facilitate motion of the knee. Muscle and tendon structures spanning the knee joint, as in other joints of the body provide dynamics to move the joint in a controlled manner while stabilizing the joint to function in an orderly fashion. Dynamic stabilization is the result of primary muscle contraction to move the joint in a desired direction combined with antagonistic muscle contraction to direct resultant joint loads within favorable orientation limits relative to the bony structures of the joint. It is believed that proprioceptive feedback provides some of the control or balance between primary and antagonistic muscle contraction.

A smooth and resilient surface consisting of articular cartilage covers the bony structures. The articular surfaces of the bony structures work in concert with the soft tissue structures to form a mechanism that defines the envelop of motion between the structures. Within a typical envelop of motion, the bony structures move in a predetermined pattern with respect to one another. When fully articulated, the motion defines a total envelop of motion between the bony structures. In the knee, the soft tissue structures spanning the joint tend to stabilize from excessive translation in the joint plane defined by the tibiofemoral joint. Such tibiofemoral stability enables the femur and tibia to slide and rotate on one another in an orderly fashion.

Current methods of preparing the intra-articular rigid elements of a joint to receive components as in joint replacement surgery involve an extensive surgical exposure. The surgical exposure, ligament release and sacrifice of the anterior cruciate ligament must be sufficient to permit the introduction of guides that are placed on, in, or attach to the joint, along with cutting blocks to guide the use of saws, burrs and other milling devices, and other instruments for cutting or removing cartilage and bone that subsequently is replaced with artificial surfaces. For knee joint replacement, the distal end of the femur may be sculpted to have flat anterior and posterior surfaces generally parallel to the length of the femur, a flat end surface normal to the anterior and posterior surfaces, and angled flat surfaces joining the above mentioned surfaces, all for the purpose of receiving a prosthetic device. In general these are referred to as the anterior, posterior, and distal and chamfer cuts, respectively. In current total knee arthroplasty proper knee alignment is attained by preoperative planning and x-ray templating. Anterior-posterior (NP) and lateral x-ray views are taken of the knee in full extension. The mechanical axis of the tibia and of the femur is marked on the NP x-ray. The angle between these lines is the angle of varus/valgus deformity to be corrected. In the A/P view, the angle of the distal femoral resection relative to the femoral mechanical axis, hence the angle of the femoral implant, is predetermined per the surgical technique for a given implant system. Similarly, the angle of the tibial resection relative to the tibial mechanical axis, hence the angle of the tibial implant, is predetermined per the surgical technique for a given implant system. The femoral resection guides are aligned on the femur to position the distal femoral resection relative to the femoral mechanical axis and the tibial resection guides are aligned on the tibia to position the proximal tibial resection relative to the tibial mechanical axis. If the cuts are made accurately, the femoral mechanical axis and the tibial mechanical axis will align in the NP view. This approach addresses knee alignment at full extension only. Knee alignment at 90° of flexion is generally left to surgeon judgment and knee alignment throughout the range of motion has not been addressed in the past. In aligning the knee at 90° the surgeon rotates the femoral component about the femoral mechanical axis to a position believed to provide proper tensioning of the ligaments spanning the knee.

Knee joint prosthesis of the type referred to above are well known, and are described, for example, in Caspari et al., U.S. Pat. Nos. 5,171,244, 5,171,276 and 5,336,266, Brown, U.S. Pat. No. 4,892,547, Burstein et al., U.S. Pat. No. 4,298,992, and Insall et al., U.S. Pat. No. 6,068,658.

Substantial effort has been made to provide appropriate degrees of curvature to the condyles in knee joint replacement. For example, the earlier mentioned U.S. Pat. Nos. 5,171,276, 4,298,992 and 6,068,658 show that the radius of curvature in the anterior-posterior direction of the condyle of a femoral prosthesis may be somewhat greater near the anterior portion of the condyle than near the posterior portion. Kester at al., U.S. Pat. No. 5,824,100 teaches that a portion of this curvature of the condyle may be formed about a constant radius having its origin along a line between the lateral and medial collateral ligament attachment points on the femur.

Historically, a variety of modular prosthetic joint implants have been developed. The following descriptions of modular implants relate specifically to the knee. Early designs for knee implants, called polycentric knee implants, were developed with separate components for the femoral and tibial surfaces of the medial and lateral tibiofemoral compartments. In this implant the patellofemoral compartment was not resurfaced. Orientating the separate components one to another, for example aligning the medial and lateral femoral components to one another, or the medial and lateral tibial components to one another, was not addressed in these designs and often left for the surgeon to make free hand resections resulting in a surgically challenging procedure. Designs emerged, such as the UCI and Gustilo knees in which the femoral condylar components were connected into an integral, unitary component as were the tibial components. The next advancement in total knee implant design was to include the patellofemoral joint by making an integral, unitary femoral component to resurface the medial and lateral femoral condyles and the patellar groove. Implants to resurface the patella were developed in conjunction with the tri-compartmental femoral components. Additionally, modular fixed-bearing knee implants, generally referred to as semi-constrained, having a polyethylene insert that is held relatively rigidly in place have been developed. Translation and axial rotation between the tibia and femur that occurs naturally with knee motion is accommodated in these designs by non-conforming tibiofemoral contact for the medial and lateral condyles. Such designs tend to have higher contact pressure which may accelerate wear and degradation of the polyethylene bearing surface. Alternately, there are mobile bearing knee implants wherein the polyethylene bearing is designed to slide or move with minimal or no constraint on a tibial baseplate. These mobile bearing designs have high conformity between the polyethylene insert and femoral condyle and the polyethylene insert and tibial baseplate resulting in lower contact stresses and a more durable design. Furthermore, both meniscal bearing and fixed bearing knee implants have been developed including either separate polyethylene bearings or a single polyethylene bearing that resides on a metallic tibial baseplate. While implant systems have been developed with fixed bearing elements or mobile bearing elements on the medial and lateral sides of the tibiofemoral joint, systems have not been developed having a combination of a fixed bearing on one side and a mobile bearing on the other side of the tibiofemoral joint.

Two primary difficulties exist with current joint replacement surgeries. These relate to the invasiveness of the procedure and achieving proper alignment and kinematics of the bony structures and the prostheses thereupon. Such difficulties are present in all total joint replacements, including ankle, knee, hip, shoulder and spine.

Alignment. A difficulty with implanting both modular and non-modular knee implants having either separate femoral and/or tibial components has been achieving a correct relationship between the components. Surgical instruments available to date have not provided trouble free use in implanting multi-part implants wherein the distal femur, proximal tibia and posterior patella are prepared for precise component-to-component orientation. While alignment guides aid in accurate orientation of opposing components relative to the axis of the long bones to achieve a restoration of a correct tibiofemoral varus/valgus alignment (usually 4-7 degrees valgus), they provide limited positioning or guidance relevant to correct subcomponent-to-subcomponent alignment in placing a plurality of components to form the articular surface of a femoral component or a tibial component and/or ligament tension to restore alignment and soft tissue balance. For the patellofemoral joint, proper tibiofemoral alignment is required to re-establish proper tracking of the patella as created by the lateral pull of the quadriceps mechanism, the articular surface of the femoral patellar groove and maintaining the tibiofemoral joint line.

While surgical instruments available to date aid in accurate varus/valgus alignment, they provide limited positioning or guidance relevant to correct flexion/extension orientation of the femoral, posterior slope of tibial components, nor of external rotation of the femoral component. For optimum knee kinematics, femoral component flexion/extension and external rotation orientation, tibial component posterior slope and ligaments spanning the joint work in concert maintaining soft tissue balance throughout the knee's range of motion.

In a properly aligned knee, the mechanical axis of the leg (a straight line drawn from the center of the hip joint to the center of the ankle) passes slightly medial to the center of the knee. This alignment is generally called the gross alignment of the leg. The alignment of the implants impacts the gross alignment of the leg. If the implants are malaligned, the resulting mechanical axis may be shifted medially or laterally, resulting in an imbalance in the loads carried by the medial or lateral condyles. This imbalance, if severe, may lead to early failure of the arthroplasty.

In the case of a plurality of sub-components resurfacing the distal femur or proximal tibia, the orientation of the sub-components to each other, for example the orientation of the medial femoral condylar sub-component to the femoral trochlear sub-component and or the lateral femoral condylar sub-component; orientation of the medial tibial component to a separate lateral tibial component; and orientation of the femoral component to its corresponding tibial component, with free standing uni-compartmental, bi-compartmental and tri-compartmental implants has largely not been addressed. This may account for the high failure rates in the surgical application of free standing compartmental replacements, used individually or in combination, and as well as for the higher failure rate of uni-compartmental implants relative to total knee implants as demonstrated in some clinical studies. When considering uni-compartmental and bi-compartmental designs, alignment of each part relative to the other parts is critical to avoid accelerated wear with a mal-articulation of the components.

Although various prosthetic devices have been successfully used with patients, the configuration and position of the articulating surfaces of the prosthesis, for example the condyles in a knee joint, are predetermined based upon the prosthesis that is selected. With a give knee implant system the implants are available in discrete sizes and the relationship, for example the ratio between medial-lateral width and anterior-posterior depth, vary between implant systems. While efforts are made to tailor the prosthesis to the needs of each patient by suitable prosthesis choice and size, this in fact is problematical inasmuch as the joint physiology of patients can vary substantially from one patient to another.

Invasiveness. In order to appropriately sculpt the articulating surface of a bone, it is often necessary to surgically expose the joint. In the case of the femur in traditional knee joint replacement, the patellar tendon of the knee joint is surgically exposed and is moved to one side of the joint and the patella everted to enable a substantially full anterior access to the joint. In general, the anterior cruciate ligament is excised to increase access to the joint space. Surgical exposure is necessary to accommodate the bulk and geometry of the components as well as the instruments for bone preparation. Such surgical exposure and ligament release or excision increases bleeding, pain, muscle inhibition and adverse kinematics; all of which contribute to a longer hospitalization before the patient can be safely discharged to home or an intermediate care facility.

Desirably, in the case of knee replacement surgery, neither the collateral ligaments nor the cruciate ligaments are disturbed, although it is often necessary to remove or release cruciate ligaments in the event a substantial joint replacement is to be performed. Collateral ligaments can be partially taken down or released to provide appropriate tension adjustment to the patient's knee in concert with joint replacement surgery. In most instances, such releases can be accomplished through smaller incisions than the standard midline or medial parapatellar incisions historically used for knee arthroplasty.

For patients who require articular surface replacement, including patients whose joints are not so damaged or diseased as to require whole joint replacement, the implant systems available for the knee have unitary tri-compartmental femoral components, unitary tibial components, unitary patellar components and instrumentation that require extensive surgical exposure to perform the procedure. It would be desirable to provide surgical methods and apparatuses that may be employed to gain surgical access to articulating joint surfaces, to appropriately prepare the bony structures, to provide artificial, e.g., metal, plastic, ceramic, or other suitable material for an articular bearing surface, and to close the surgical site, all without substantial damage or trauma to associated muscles, ligaments or tendons, and without extensive distraction of the joint. To attain this goal, implants and instruments are required to provide a system and method to enable articulating surfaces of the joints to be appropriately sculpted using minimally invasive apparatuses and procedures and to replace the articular surfaces with implants suitable for insertion through small incisions, assembly within the confines of the joint cavity and conforming to prepared bone support surfaces.

SUMMARY OF THE INVENTION

The present invention provides a system and method for total joint replacement that is to resurface each bony surface of the joint or motion segment that involves minimally invasive surgical procedures including an implant system that restores individual patient's joint kinematics. As used herein, the following terms have the following definitions.

Minimally invasive or less invasive—For the purposes of the present invention an incision for conventional total knee arthroplasty is defined as being generally greater than 6 inches in length. An incision for minimally and less invasive knee arthroplasty is defined as being generally less than 6 inches in length.

Engage—For the purposes of the present invention engage pertains to 1) engagement of sub-components of an implant to form the implant, and 2) engagement of implant components of a joint arthroplasty. In both cases engage means to cause mechanical parts (i.e. sub-components of a femoral component for example, or a set of components to include femoral, tibial and patellar components for example) to come together, to mesh to one another, to interlock with one another, or to come into working contact with one another. Such contact between adjoining parts limiting at least one degree of freedom between the parts.

Joining—For the purposes of the present invention joining pertains to joining of subcomponents of an implant to form the implant and means to cause mechanical parts (i.e. sub-components of a femoral component for example) to be interlocked together so as to form a unit.

Orienting—For the purposes of the present invention orientating pertains to 1) orientating sub-components of an implant to one another, and 2) orientating implant components of a joint arthroplasty to one another. In both cases orientating means to bring the parts into working relationship to one another so that the assembly of parts functions as intended.

Aligning—For the purposes of the present invention aligning pertains to 1) alignment of sub-components of an implant to supporting bone, and 2) alignment of implant components of a joint arthroplasty to supporting bone. In both cases aligning means to bring the parts into correct relative position with respect to the supporting bone so that the arthroplasty functions as intended.

Implant component and sub-component—For the purposes of the present invention an implant component refers to the parts that make up the arthroplasty, for example femoral, tibial and patellar components make up a total knee arthroplasty. Sub-component refers to the parts that make up the implant component. Each component may be unitary in construction, or may include a plurality of sub-components.

For the purposes of describing the invention, arthroplasty includes total and partial joint replacement (i.e. hip, knee, shoulder, ankle, finger joints, etc.) and total and partial spinal disc and facet replacement. Such arthroplasty systems include components such as femoral, tibial and bearing insert components for a knee arthroplasty; stem, head, bearing insert and shell components for a hip arthroplasty; and vertebral endplate and bearing insert for spinal arthroplasty.

The instruments and implants disclosed accomplish accurate bone and soft tissue preparation, restoration of anatomical alignment, soft tissue balance, kinematics, component to component orientation and alignment, sub-component to sub-component orientation and alignment, and implant fixation through limited surgical exposure. For knee joint replacement, the implant system is comprised of implants that provide intraoperative surgical options for articular constraint and facilitate proper alignment and orientation of the knee to restore anatomical alignment, soft tissue balance and kinematics as defined by individual patient anatomy. To do so, the implants provide the surgeon intraoperative options to reconstruct various degrees of joint stability via selection of fixed or mobile bearing components for each compartment of the knee (medial tibiofemoral, lateral tibiofemoral and patellofemoral compartments). The range of implants may be applied to one, two or three of the knee joint compartments in a given procedure and may include combinations of fixed and mobile bearing configurations.

In conventional total knee replacements, the femoral component is typically a unitary piece and the tibial component is a unitary piece. A bearing is placed between the femoral and tibial components, typically a unitary piece that may be fastened to the tibial component or sliding on the tibial component. In the present invention, the femoral side may be resurfaced by two, three or more distinct sub-components and the tibial side may be resurfaced by two distinct sub-components or a unitary piece. The modular femoral component comprised of two or three distinct sub-components is sized to be placed through a minimally invasive incision into the joint space one piece at a time and assembled therein during the surgical procedure. Likewise, the modular tibial component comprised of one or two polyethylene bearings and a baseplate component comprised of two or three distinct sub-components each of which is sized to be placed through a minimally invasive incision into the joint space one piece at a time.

In an alternate embodiment distinct femoral sub-components and tibial sub-components may be interconnected with flexible interconnection means such as one or more spring elements, wires, flanges or hinges to enable bending the construct to facilitate passage through a small incision when the sub-components are joined outside the joint space (i.e. when preassembled). Alternatively, the sub-components can be inserted through the incision individually and the flexible interconnection means used to join the subcomponents within the joint space. After the sub-components have been joined with the flexible interconnection means and after placement in the joint cavity, the flexible interconnection means also assist in repositioning the components onto the kinematically prepared bone surfaces. Flexible interconnection means may be made from a suitable alloy to include, but are not limited to, NP35N or Nitinol, or polymers to include, but limited to, polyethylene or Gore-Tex.

Alternatively, the multi-piece tibial component may have a stem that can be placed individually into the joint space and designed to pass down the tibial medullary canal and attach to the baseplate or baseplate sub-components within the confines of the joint space. Likewise, the modular femoral component may have a stem that can be placed individually into the joint space and designed to pass down the femoral medullary canal and attach to the femoral subcomponents.

The femoral sub-components are accurately orientated to one another after placement in the joint cavity before or after interconnecting the individual sub-components with the flexible interconnecting means. Likewise, the tibial sub-components are accurately orientated to one another in the same manner. In both cases, the size of each component or sub-component passed into the joint is significantly reduced compared to conventional components enabling completion of the procedure through a smaller and less traumatic exposure. The sub-components may be aligned and or joined one to another within the confines of the joint, such pieces being properly orientated, but not joined within the joint cavity. Alternatively, the independent femoral subcomponents may be properly orientated and joined within the joint cavity. Likewise, the tibial component may be distinct pieces to cover the medial and lateral tibial plateaus, such pieces being properly orientated, but not joined within the joint cavity. Alternatively, the distinct tibial pieces may be properly orientated and joined within the joint cavity. The patellar component is generally of a size, i.e. from X to Y, that can be placed through minimally invasive incisions as a unitary bearing, fixed bearing or mobile bearing component. In one aspect of the present invention, the articular surface of the patellar component may comprise independent, distinct pieces for the lateral facet and medial facets which are properly orientated, but not joined within the joint cavity. In yet another aspect of the present invention, the independent patellar pieces may be properly orientated and joined within the joint cavity. In still another aspect of the present invention, the femoral component may be flexible or include flexible sub-components.

Proper alignment and positioning of the implant components and sub-components are enabled by instruments guided by the soft tissue structures of the knee to guide bone resections for patient-specific anatomical alignment and component orientation. The medial and lateral tibial articular surfaces and the patellar articular surface are generally prepared with planar resections. The medial and lateral femoral condyles and trochlea are kinematically prepared. Such instrumentation is referred to as Tissue Guided Surgery (TGS) and is described in U.S. Pat. No. 6,723,102.

Femoral, tibial and patellar bone resections attained with TGS instrumentation are properly positioned and orientated for anatomic knee alignment, soft tissue balance and kinematic function throughout knee range of motion. Using these bone support surfaces to position and orientate the femoral, tibial and patellar components, respectively, will maintain anatomic knee alignment, soft tissue balance and kinematic function. In general, the tibial and patellar resections are planar making placement of the corresponding implant components, which have planar support surfaces, straight forward. The femoral resection is not planar and the relative position of the lateral condyle, the medial condyle and the trochlear resections to one another is a function the kinematics of a given patient. Therefore, the femoral implant must accommodate this variability, as described herein.

Given that the soft tissue structures spanning the knee are used to guide the TGS instrumentation it is beneficial for such tissues to be minimally disrupted by the surgical technique and to avoid dislocation or eversion of the patella. The minimally invasive surgical incision or incisions used to access the knee joint must be of a size and orientation relative to the soft tissue structures that minimizes alteration of knee kinematics. The femoral, tibial and patellar implants must be designed to pass through such minimally invasive incisions. Conventional femoral and tibial implants for total knee arthroplasty are sized so large that insertion through a minimally invasive incision is not feasible. In addition, the shape of conventional femoral components does not permit placement of the component over the resected distal femur with the majority of soft tissues intact or without dislocation or eversion of the patella. Further, the confines of the joint cavity do not provide sufficient space to align conventional femoral components distal to the anterior and posterior femoral resections and then slide the component over those resections. Therefore, the femoral, tibial and patellar components must be sized to be passed through a small incision and to be placed onto or over the respective bone support surfaces. For the femoral component, one embodiment is a component made up of a plurality of sub-components to resurface the medial condyle, the lateral condyle and the trochlea of distal femur. Such sub-components are of a size that can be passed through a small incision and be assembled, that is joined or engaged, within the confines of the joint cavity.

Femoral sub-components conform to the shape of the kinematically prepare condyles and trochlea. The interfaces between femoral sub-components are partially constrained. These interfaces are unconstrained in angulation generally in a sagittal plane to allow the subcomponents to conform to the trochlear and condylar resections. These interfaces are constrained in angulation generally in a transverse plane, in orthogonal and axial translation and in axial rotation to provide a smooth transition from one sub-component to an adjacent subcomponent. A smooth transition provides uniform support for the mating tibial or patellar component. Alternatively, the interfaces between the femoral sub-components are unconstrained in angulation and constrained in other degrees of freedom to allow the femoral component to conform to the resected femoral condyles and to vary the anteroposterior divergence of the condyle sub-components with a similar divergence in tibial sub-components. Alternatively, the interfaces between the femoral sub-components are fully constrained. Likewise, tibial subcomponents are properly aligned with one another to ensure proper tracking of the femoral, tibial and patellar components.

In addition to preparing the bone for patient-specific alignment and orientation of the implant components, the present invention provides further component orientation by joining the femoral sub-components together and joining the tibial sub-components together. The femoral sub-components may be temporarily or permanently joined after being placed into the joint space. Likewise, the tibial sub-components may be temporarily or permanently joined after being placed into the joint space. When the sub-components are to be temporarily joined within the joint space one or more brackets are interposed between the sub-components and secured to each sub-component. The brackets hold the sub-components in proper alignment to each other while the component is secured to bone by mechanical means such as bone screws, spikes, hooks, etc., or bone cement, or other bonding material. The bracket or brackets are removed after the components are secured to the supporting bone.

In the case of knee replacement surgery, the implants include a second bone baseplate, a bearing insert and a first bone implant. The second bone baseplate may be either one piece to cover most of the prepared surface of the second bone as relates to the joint, or separate baseplates as have been used with mobile or fixed bearing prosthetic components. In both one piece and two piece baseplates the bearing insert may be one piece supported by a one piece baseplate or by each component of a two piece baseplate. Alternately, the bearing insert may be two piece separate inserts supported by a one piece baseplate or individually by each subcomponent of a two piece baseplate. In addition, the second bone baseplate may accommodate separate fixed and mobile bearing inserts used in medial and lateral combinations of fixed-fixed, mobile-fixed, fixed-mobile and mobile-mobile bearing inserts, respectively. In the case of separate baseplates that are joined together, such joining is through a partially constrained interface. In one aspect of the present invention, the sub-components are joined together through a fully constrained interface. Such joined sub-components being assembled within the confines of the joint cavity then secured to supporting bone. In another aspect of the present invention, such joined sub-components being secured to supporting bone then assembled within the confines of the joint cavity. In yet another aspect of the present invention, such joined sub-components are assembled and passed through a small incision into the joint cavity, then positioned and secured on the second bone. In all cases, the tibial implants are designed to be passed through a small or minimally invasive incision or through multiple minimally invasive incisions.

As with the second bone implant, the first bone implant is comprised of a plurality of sub-components to replace the bearing surface of the first bone, such sub-components being joined together within the confines of the joint cavity. In the case where the first bone is the distal femur the sub-components include medial and lateral condylar sub-components and a trochlear sub-component. The interfaces between the sub-components can be partially constrained, fully constrained, or a combination thereof. Each sub-component is individually passed through the small incision into the joint cavity. The sub-components are assembled within the confines of the joint cavity and then secured to the femur. Alternatively, the subcomponents are individually secured to the femur and then assembled.

It may be advantageous to partially assemble the femoral implant outside the joint cavity, for example passing the medial condylar sub-component into the joint cavity then assembling the lateral condylar sub-component to the trochlear sub-component and passing the assembly into the joint cavity to engage the medial condylar sub-component. The trochlear to medial condylar sub-component interface is then assembled and the femoral component secured to the femur. Alternatively, the medial condylar sub-component is placed into the joint cavity and secured to the femur, and then the trochlear and lateral condylar sub-components are assembled and passed into the joint cavity to engage the medial condylar sub-component and secured to the femur. Alternatively, the medial and lateral condylar sub-components are individually passed into the joint cavity and held in position with a bracket connected to both sub-components. The medial and lateral condylar sub-components are secured to the femur, the bracket is removed and the trochlear sub-component is passed into the joint cavity to engage the medial and lateral subcomponents, assembled and secured to the femur.

In the case of separate baseplates that are not joined together, it is beneficial to have a bracket that attaches to the pieces to hold the pieces properly orientated one to another while they are secured to the supporting bone. Means to attach the bracket to the pieces include threaded fasteners, clamping devices, tether cable or wire attachments, or a combination of these, or other fastening means used to connect two or more parts.

The first bone implant is comprised of a plurality of sub-components to replace the bearing surface of the first bone. In the case where the sub-components the femoral component are properly orientated and joined within the joint, fastening means used to join the distinct pieces together include threaded fasteners, cylindrical pins, conical taper locks, square or rectangular taper locks, tether cable or wire locks, a combination of the foregoing, or any such other fastening means that can be used to connect two or more parts. In the case where the pieces are not joined together, it is beneficial to have a bracket that attaches to the pieces to hold the pieces properly orientated one to another while they are secured to the supporting bone. Means to attach the bracket to the pieces includes threaded fasteners, clamping devices, tether cable or wire attachments, or a combination of these, or other fastening means used to connect two or more parts. Optionally, a portion of the first bone implant may be configured of a plurality of flexible segments bonded in place. Such a configuration permits the articulation of the second bone to the first bone to mould the flexible segments in appropriate position. Alternatively, the femoral sub-components as previously described may be configured as flexible sub-components to be joined within the confines of the joint cavity and secured to the femur. Alternatively, the femoral component may be of unitary construction in which the component is flexible. In all cases, the femoral implant is designed to be passed through a small or minimally invasive incision into the joint cavity.

The use of tethering means is advantageous for guiding subsequent sub-components into the joint cavity and onto a mating sub-component. Tethering means include wires, cables, lines, filaments, sutures, braids, tape, threads, strands, cords and other such devices so long as it provides sufficient strength and flexibility to support the components and the passage of the components into the joint space, and aid in aligning and positioning the sub-components into the joint space. In one embodiment of the present invention an implant or surgical instrument includes tethering means to facilitate the passage of the implants and or instruments through a surgical incision to a desired location and position within the body. The tethering means includes an attachment end and a receiving end and includes a body portion running along the longitudinal axis of the tethering means between the respective ends. The attachment end may be attached to soft tissue and or bony structures within the body. Preferably, the attachment end is attached to an implant or instrument and said implant or instrument attached to soft tissue and or bony structures within the body. Alternatively, the implant or instrument may be placed within the body. Optionally, the tethering means may be temporally or permanently attached to said implant or instrument. The attachment end of the tethering means is passed through the minimally invasive incision with the longitudinal body portion and the receiving end remaining outside the body. The receiving end is designed to receive subsequent implants or instruments that are placed over the tethering means and advanced through the incision. In operation, a first implant component or sub-component is placed within the confines of the joint cavity as disclosed herein and the attachment end of the tethering means is attached thereto. A second implant component or sub-component is threaded over the receiving end of the tethering means and is guided along the body portion through the minimally invasive incision and into the joint space in proximity to the first implant component or sub-component. The tethering means may have a circular, oval, square, or rectangular cross section or any other suitable cross section over which a second implant may be passed. Tethering means with a circular cross section is desirable if the second implant is not required to be rotationally orientated to the first implant. Tethering means with a circular cross section or a second implant with a clearance hole large enough to allow rotation around the tether allows rotation of the second implant to ease or facilitate passage over the tethering means and or through openings through which the tethering means has been passed. Tethering means with a non-circular cross section in combination with a second implant with a matching through hole is desirable to control rotational orientation of said second implant to said first implant allowing for joining of unique engagement features at the interface between second and first implants without visualization or other means to guide said second implant towards said first implant and to engage, join and or assemble said second implant with said first implant. In addition, the tethering means may be part of a locking means to secure said second implant to said first implant, or the tethering means may be removed after the second implant has been guided into position. The tethering means may be made of metal, polymer, plastic or other suitable material and may be pre-attached to the first implant during manufacture, or it may be attached to the first implant at the time of surgery. One or more tethering means may be used to guide said second implant towards said first implant allowing for a plurality of implants to be guided towards the preceding implant. Likewise, two or more implants may be guided towards one implant over two or more tethering means. Conversely, one implant may be guided towards two or more implants over two or more tethering means. The first, second or multiple implants described above may be sub-components of an orthopaedic or spinal implant for joint arthroplasty, spinal surgery or trauma fixation.

The placing, guiding and securing of three sub-components of a modular femoral component with tethering means in accordance with the present invention will now be described. A tethering means is attached to the medial condylar sub-component and a second tethering means is attached to the lateral condylar sub-compartment. Each condylar sub-component is individually passed through the small or minimally invasive incision, positioned and secured to the femur; leaving its respective tethering means extending out of the incision. Each tethering means is passed through its corresponding through hole in the trochlear sub-component and the trochlear sub-component is advanced over the tethering means which guide the trochlear sub-component through the minimally invasive incision and into the joint cavity. The tethering means further guide the trochlear sub-component to join with the medial and lateral condylar sub-components. A tensioner is attached to each tethering means and applies a compressive force to the trochlear sub-component thereby joining or engaging the femoral sub-components. Each tethering means is then secured to the trochlear sub-component and excess tether trimmed. This aspect of the present invention enables the placement of implant sub-components into the joint cavity through a small or minimally invasive incision, joining of such sub-components within the confines of the joint cavity, assembly of such sub-components within the confines of the joint cavity and securing such sub-components to one another.

The implant and tethering means combination for placing sub-components is applicable to the femoral, tibial, patellar and bearing insert components of a knee implant. In addition, this embodiment of the present invention is applicable to other joint implants, including but not limited to hip, shoulder, fingers and ankle; to spinal implants including but not limited to spinal disc replacement, facet replacement and spinal fusion; and to orthopaedic trauma products to include but not limited to fracture fixation systems.

Optionally, the tibial component is designed for use with a tibial stem for anchorage in the tibial canal. Current modular tibial components that include a baseplate and stem are designed for assembly outside the joint cavity. The available space within the knee joint cavity when accessed through a small or minimally invasive incision is not adequate to place an assembled baseplate and stem. In addition the interface between the baseplate and stem generally used in current modular tibial components requires more room than is available in the joint cavity when accessed through a small or minimally invasive incision. In the present invention the interface between tibial baseplate and tibial stem allows placement of the stem through a small or minimally invasive incision and into the tibial canal followed by placement of the baseplate. The stem and baseplate are joined within the confines of the joint cavity. The interface between the baseplate and stem allows the baseplate to be placed over the proximal aspect of the stem, slide into engagement and lock to the stem. Optionally, the interface between the baseplate and stem allows the baseplate to be passed through a: small or minimally invasive incision and onto the resected tibial followed by placement of the stem into the joint cavity and through a receiving feature on the baseplate then into the tibial canal. The stem and baseplate are joined within the confines of the joint cavity. The interface between the baseplate and stem allows the stem to pass through the baseplate, slide into engagement and lock to the baseplate. Alternatively, the various embodiments of the tibial component described herein can be adapted for use with the modular tibial stem in both the stem first and baseplate first embodiments of the baseplate and stem configuration. In addition, the femoral component embodiments described herein can be configured for use with a femoral stem in a manner similar to that of the tibial baseplate and tibial stem construct. Likewise, the femoral components described herein can be adapted for use with a modular femoral stem in both stem first and femoral component first embodiments.

Specifically, for example in knee joint replacement, the invention may be used for replacing the surfaces of a femur, a tibia, a patella, or a combination of these. Thus, a femoral implant having a plurality of sub-components, a tibial baseplate having a plurality of subcomponents and a patellar component having a plurality of sub-components are provided. The tibial baseplate components and the patellar components may have fixed bearing attachments as well as mobile bearing attachments. Optionally, each component of the tibial baseplate or patellar may have a fixed bearing attachment as well as a mobile bearing attachment. Alternatively, the tibial component and the bearing attachment may be of unitary construction and the patellar component and bearing attachment may be of unitary construction. Optionally, the femoral and tibial components of the invention may be used with modular femoral and tibial stems, respectively.

DETAILED DESCRIPTION

Knee Joint Anatomy and Surgical Approaches.

Figure 1:
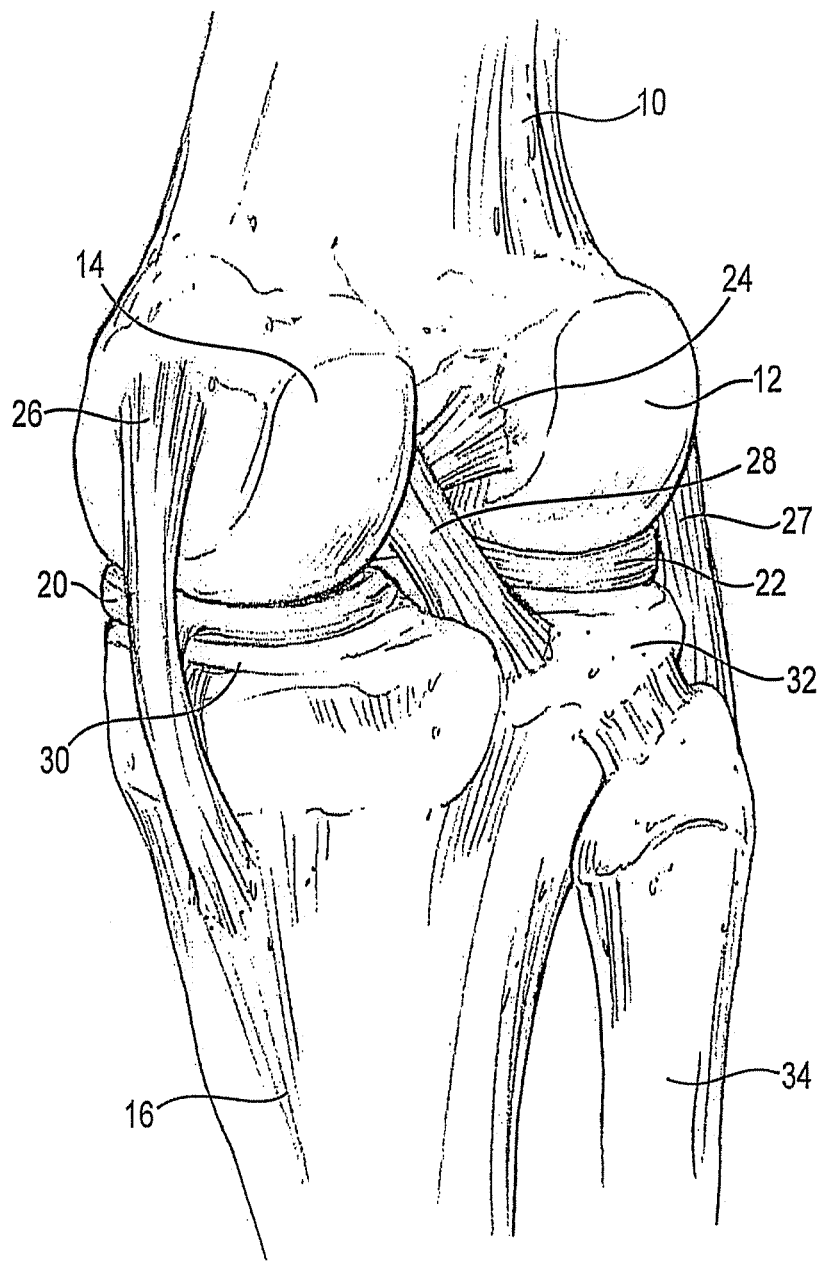
FIG. 1 is a plane view of a knee joint.

FIG. 1 illustrates the general anatomy of the knee joint. The femur 10 has the lateral femoral condyle 12 and the medial femoral condyle 14 on its knee-joint articulating surface. The tibia 16 has the lateral meniscus 22 (generally opposite the lateral femoral condyle 12) and the medial meniscus 20 (generally opposite the medial femoral condyle 14) on its knee-joint articulating surface. The ligaments include the anterior cruciate ligament 24, the posterior cruciate ligament 28, the medial collateral ligament 26 and the lateral collateral ligament 27. The medial tibial condyle 30 and the lateral tibial condyle 32 support the menisci 20 and 22, which in turn support the femur 10. Additionally, the fibula 34 engages the tibia 16.

Typically, a total knee joint replacement involves replacing the articular surfaces of the lateral femoral condyle 12, the medial femoral condyle 14, the medial tibial condyle 30 and the lateral tibial condyle 32. The lateral meniscus 22 and the medial meniscus 20 are removed. Desirably, neither the collateral ligaments 26 and 27 nor the cruciate ligaments 24 and 28 are disturbed. However, the collateral ligaments 26 and 27 may be partially taken down to provide appropriate tension adjustments to the patient's knee after joint replacement has been completed. Such structures are contained within the intact knee joint cavity which is formed by the knee synovial bursa (not shown).

Figure 2:
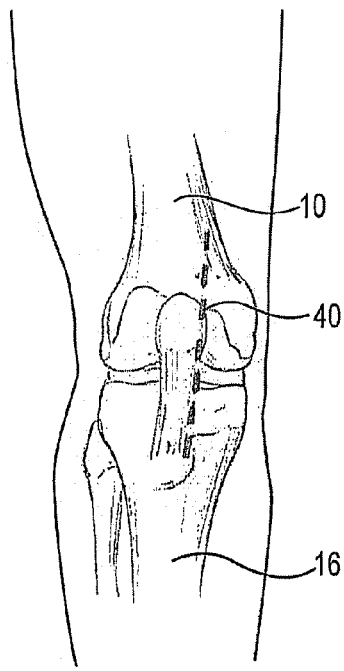
FIG. 2 illustrates a traditional midline incision for accessing the knee joint during total knee replacement surgery.

Referring to FIG. 2, the conventional midline incision 40 for a total knee replacement surgery is shown. The incision 40 extends vertically substantially above and below the articulating surface between the femur and the tibia. Typically, the incision is roughly 8 to 15 centimeters in length. The incision 40 must be large enough to expose the entire knee joint articular surfaces with the patella subluxed or dislocated. Additionally, the incision must accommodate insertion of components that fully cover the end of the femur, the top of the tibia and the undersurface of the patella. The maximum number of components implanted would include femoral and tibial components for the lateral tibiofemoral compartment, femoral and tibial components for the medial tibiofemoral compartment and femoral and patellar components for the patellofemoral joint. Alternatively, the lateral femoral condyle and the patellar groove may be covered by a common implant. The knee joint cavity is substantially opened by the incision 40 and the exposed articular surfaces of the knee protrude out of the joint cavity to accommodate current bone resection instruments and insertion of components that fully cover the end of the femur, the top of the tibia and the undersurface of the patella.

Figures 3, 4:
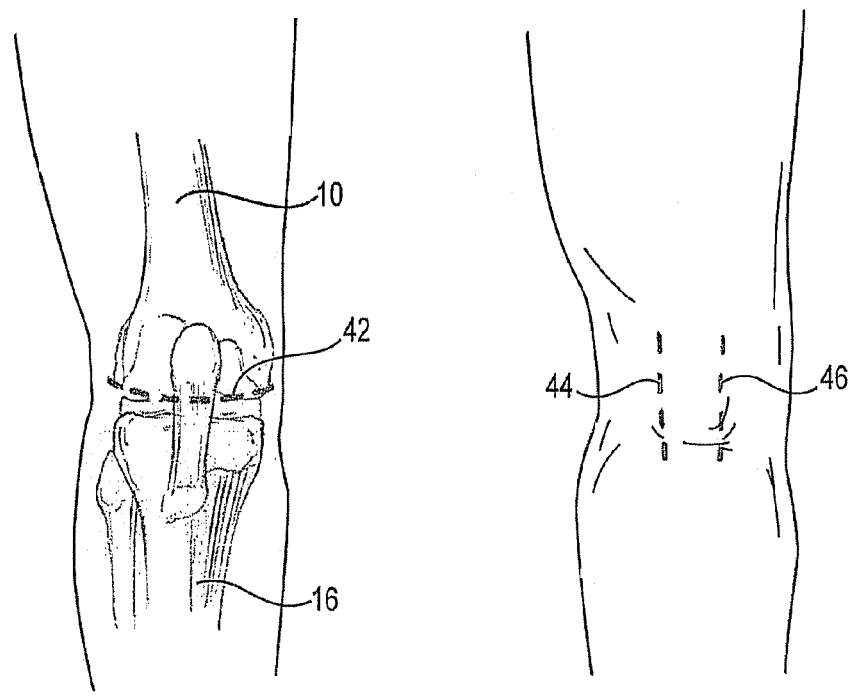
FIG. 3 depicts an incision for accessing the knee joint during total knee replacement surgery that may be used with the method and apparatus of the present invention.
FIG. 4 illustrates alternate incisions for accessing the knee joint during total knee replacement surgery that may be used with the method and apparatus of the present invention.

As best seen in FIG. 3, a transverse incision 42 extending horizontally along the knee joint is one option for the procedure of the present invention. The incision 42 may be vertically opened to expose the joint surfaces of the medial tibiofemoral compartment and the lateral tibiofemoral compartment without dislocating the patella. This maintains the patella in contact with the femur during the procedure. The components of the instrumentation as well as the implant are sized for minimal invasiveness and, therefore, may be accommodated by the small incision. The reduced trauma resulting from a smaller incision generally results in faster and better rehabilitation, which in turn generally increases the efficacy of the knee implant.

Referring to FIG. 4, an alternate incision format for use with the present invention is shown. Two parallel vertically extending incisions 44 and 46 may be formed on either side of the patella. These incisions 44 and 46 are relatively short and the invasiveness is similar to that of the horizontal incision in FIG. 3. Each incision 44 and 46 is separately extended through the joint capsule to expose the medial and lateral tibiofemoral compartments without dislocating the patella.

Figure 5:
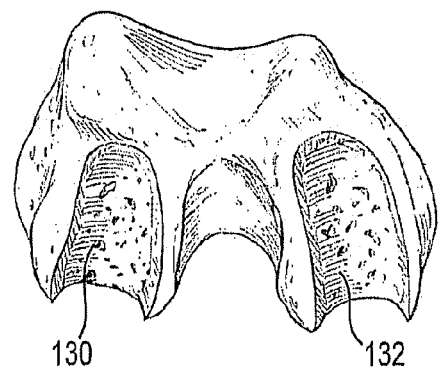
FIG. 5 is a plane view of femoral resections made in accordance with an embodiment of the present invention.
Figure 6:
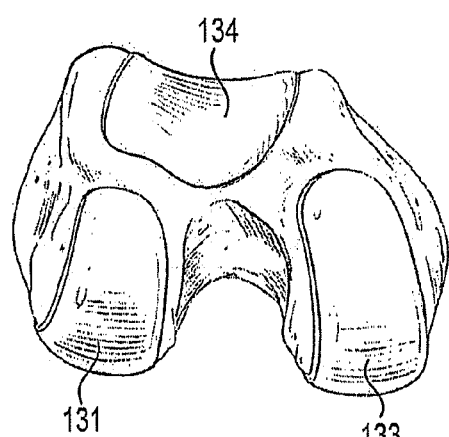
FIG. 6 is a plane view of femoral resections made in accordance with an alternate embodiment of the present invention containing femoral implants.
Figure 7:
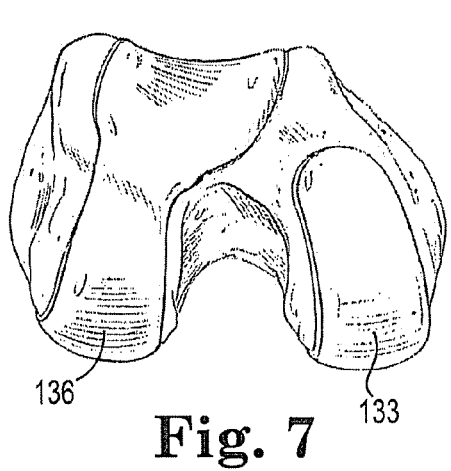
FIG. 7 is a plane view of femoral resections made in accordance with a yet another embodiment of the present invention containing femoral implants.

FIG. 5 shows the bone resections 130 and 132 in the femoral condyles. FIGS. 6 and 7 depict alternate embodiments of the bone resections in the femoral condyle as may be desired.

Implants.

The surgical procedure is preferably performed through minimally invasive incisions that do not necessitate subluxation or dislocation of the patella. Therefore, implants such as the femoral, tibial or patellar implants are designed that may be fit through minimally invasive incisions, conformed to the kinematically prepared bone support surfaces, and either oriented or joined within the joint. The femoral and tibial implants may be attached to bone with conventional bonding methods such as, but not limited to, polymethylmethacrylate, or by direct attachment to bone as with, but not limited to, a porous ingrowth surface.

Figure 9:
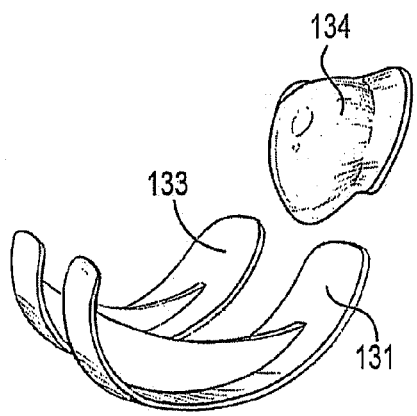
FIG. 9 is a plane view of femoral implants for resurfacing the femoral resections of FIG. 6 according to an embodiment of the present invention.
Figure 10:
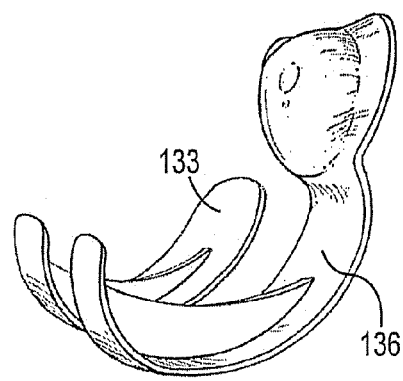
FIG. 10 is a plane view of femoral implants for resurfacing the femoral resections of FIG. 7 according to an embodiment of the present invention.
Figure 11:
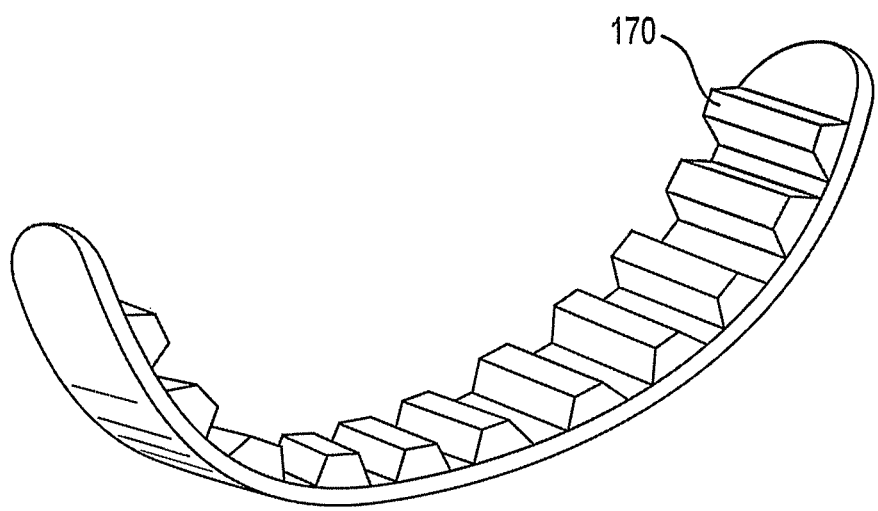
FIG. 11 is a plane view of a femoral implant in accordance with an embodiment of the present invention.

It is preferable to place all of the implants through small incisions. As seen in FIG. 9, the femoral implants include a first sub-component 131 to resurface the articulating surface of the medial condyle and a second sub-component 133 to resurface the articulating surface of the lateral condyle and a third sub-component 134 to resurface the femoral trochlea. Optionally, as seen in FIG. 10, the femoral implants may include a first sub-component 133 to resurface the articulating surface of the lateral condyle and a second sub-component 136 to resurface the articulating surface of the lateral condyle and the femoral trochlea. FIG. 11 is an illustration of an optional femoral condyle sub-component configured as a flexible implant. The outer surface of the condylar implant is a thin sheet of material and the inner surface may be ridged 170.

Figure 8:
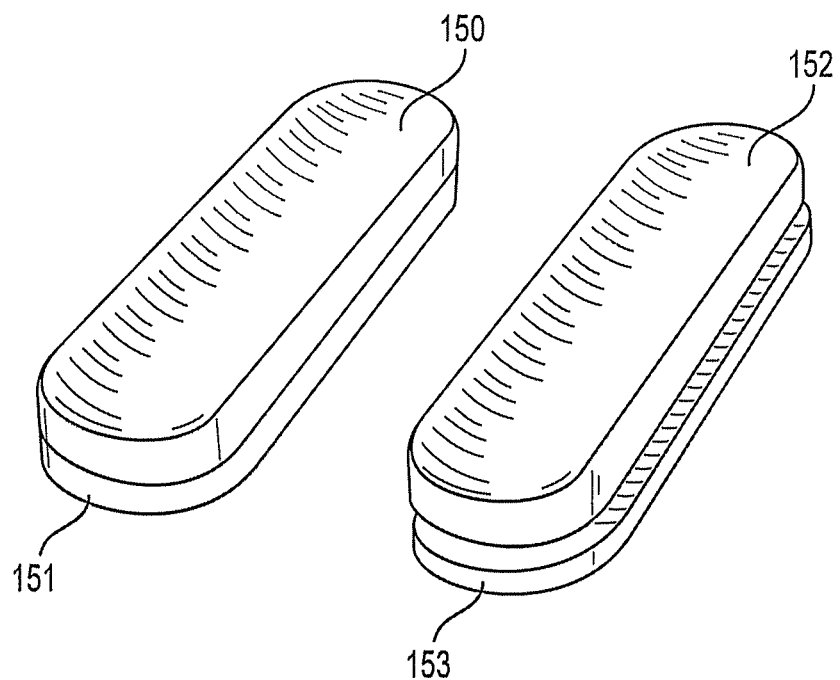
FIG. 8 are plane views of alternate embodiments of tibial baseplates in accordance with an embodiment of the present invention.
Figure 20:
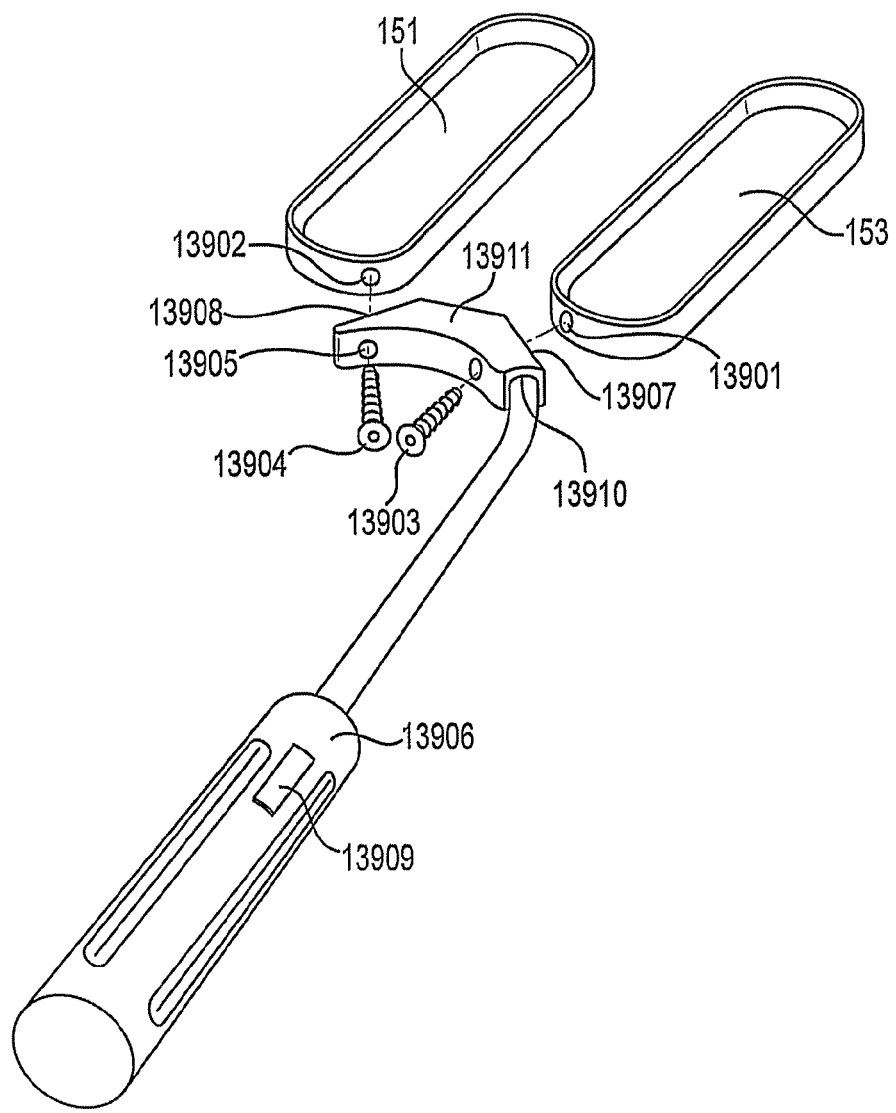
FIG. 20 illustrates an instrument for placing and aligning a two piece tibial baseplate that is not joined according to an embodiment of the present invention.

Alternatively, as depicted in FIG. 8, the tibial implants may be configured as separate plateau baseplates for the medial and lateral compartments. In one embodiment of the present invention these sub-components are oriented one to the other by an alignment instrument or bridge that dictates their orientation in relationship to each other and/or to the femoral components. As can be seen in FIG. 20, the medial baseplate sub-component 153 and the lateral baseplate sub-component 151 have threaded receiving holes 13901 and 10912 anteriorly. The bridge 13911 contains two threaded fasteners 13903 and 13904 to attach the bridge to the each of the baseplate sub-components 153 and 151. Preferably, the bridge 13911 is assembled to the handle 13906 and the medial baseplate 153 outside the joint cavity. In the case of cement being used to secure the baseplates 151 and 153 to the tibia, cement is applied to the medial and lateral baseplates 153 and 151. Trial femoral sub-components (not shown) are placed on the lateral and medial femoral condyles and trial insert bearings (not shown) are placed on the lateral and medial baseplates 151 and 153. The lateral baseplate 151 is placed into the lateral compartment of the knee. The medial baseplate 153 is placed into the medial compartment with the aid of the handle 13906 until the lateral threaded fastener 13904 can be threaded into the receiving hole in the lateral baseplate 151. The contact surfaces between the bridge 13911 and the medial 153 and lateral 151 baseplates is contoured for a fully constrained lock between the bridge 13911 and baseplate sub-components 153 and 151. Optionally, the handle 13906 is designed with an alignment guide (not shown) to reference the mechanical axis of the knee to aid in aligning the tibial components. The knee is extended to load the implants and excess cement is removed. The handle 13906 may be removed and the bridge 13911 left in place to improve access to the joint cavity for cement cleanup. The handle 13906 is removed by releasing the lock switch 13909 which releases the dovetail interlock 13910 connecting the handle 13906 to the bridge 13911. Once the cement has set the bridge 13911 is removed.

Figure 12:
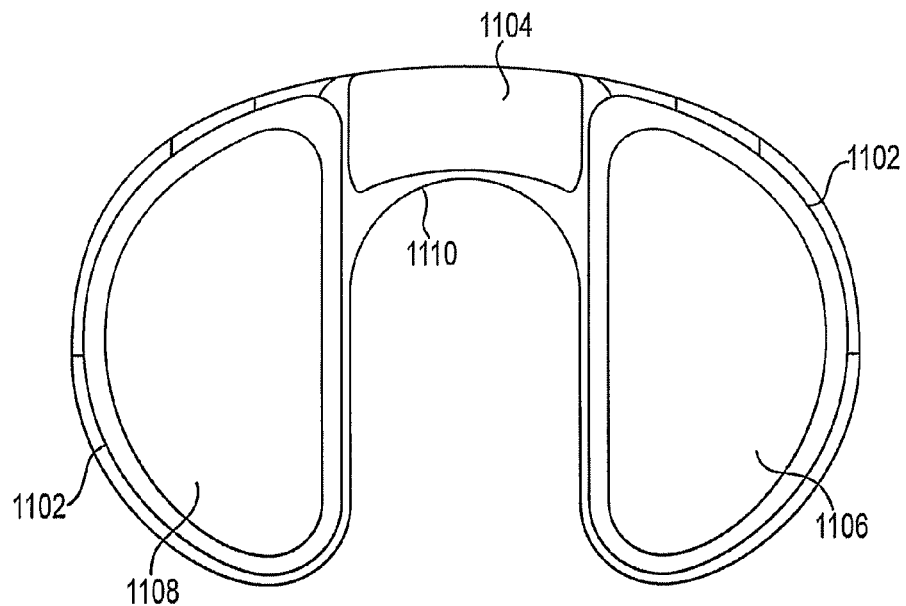
FIG. 12 is a plane view of a tibial implant with unitary baseplate according to an embodiment of the present invention.

As shown in FIG. 12, the tibial baseplate is optionally configured as a unitary component to cover most of the prepared surface of the tibial plateau as relates to the knee. The medial baseplate 1108 and lateral baseplate 1106 may be symmetrical to allow use of one design for right or left knees. Alternatively, the medial baseplate 1108 and lateral base 1106 may be asymmetric requiring left and right designs. The bridge 1104 between the medial 1108 and lateral 1106 baseplates is shown with a narrow anterior to posterior dimension to enable placement of the bridge 1104 anterior to the insertion of the anterior cruciate ligament to preserve supporting bone in an anterior cruciate sparing total knee design. Optionally, the posterior surface of the bridge 1110 may be moved posteriorly (not shown) for an anterior cruciate sacrificing total knee design. Optionally, the posterior surface of the bridge may be moved further posteriorly (not shown) for a cruciate sacrificing (anterior and posterior cruciate ligaments) total knee design, commonly known as a posterior stabilized total knee. The proximal surfaces of the medial 1108 and lateral 1106 baseplates are recessed with a shoulder 1102 around the circumference of the recess providing one form of capture mechanism or restraint for a tibial bearing insert (not shown). Other tibial bearing insert to baseplate locking means are known in the art and include dovetail mechanism, locking tabs, locking keys and pins and other fasteners to secure a tibial bearing insert onto a baseplate.

If configured as a unitary component, the tibial baseplate provides a capture mechanism for a fixed bearing or a mobile bearing insert for either the medial or lateral tibiofemoral compartment. As an option, a single platform is designed that provides a fixed bearing capture mechanism for the medial tibiofemoral compartment and a mobile bearing capture mechanism or a simple platform to receive a mobile bearing insert for the lateral tibiofemoral compartment. Since right and left tibial baseplates are required, the same baseplate may be used for a mobile bearing medial insert and a fixed bearing lateral insert.

Figure 13:
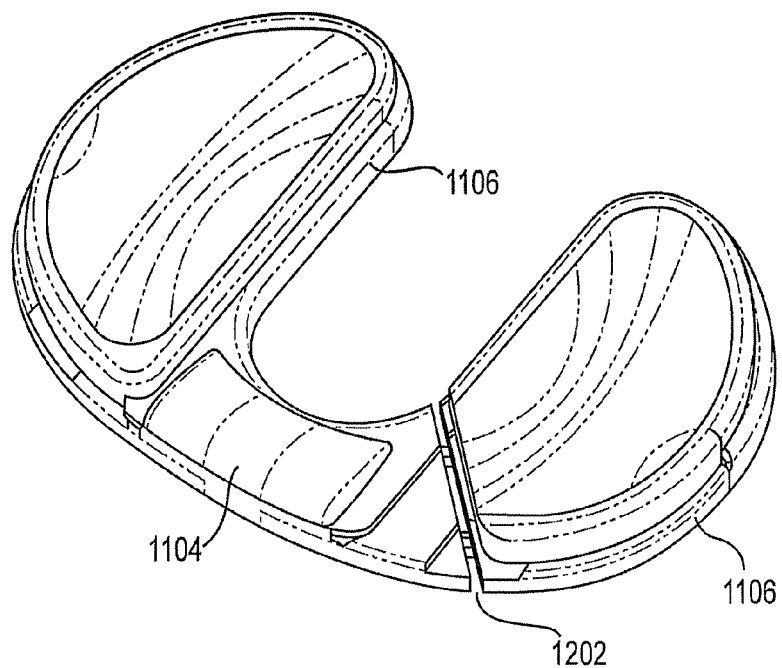
FIG. 13 is an orthogonal view of a tibial implant with a two piece joined baseplate according to an embodiment of the present invention.

As shown in FIG. 13, the tibial baseplate is optionally configured as a two piece component wherein the sub-components are joined within the confines of the joint cavity. The split 1202 between the medial baseplate 1108 and lateral baseplate 1106 is preferably medial of the bridge 1104; however the split 1202 may be located anywhere along the bridge and angle medially or laterally with respect to the sagittal plane, or be parallel to it. The benefit of placing the split 1202 medially and angled is three fold, first this provides additional cross sectional area for an interconnect mechanism, second it provides easy access perpendicular to the split 1202 via the medial parapatellar incision for fastener placement, and third it provides an extension onto which an inserter can be attached to facilitate placement of the lateral tibial baseplate subcomponent 1106 through a medial parapatellar incision. Preferably, the interconnection between the medial baseplate sub-component 1108 and the lateral baseplate sub-component 1106 at split 1202 is fully constrained to hold the medial 1108 and lateral 1106 sub-components in a common plane and to hold the divergence of the sub-components at a fixed angle. Optionally, the interconnection at split 1202 is partially constrained. In an anterior cruciate ligament sparing knee the medial and lateral tibial resections are generally made independently which may induce regional variations in the contour of the supporting bone surface. For the tibial component such variations are minimal. Nonetheless, it is advantageous to accommodate such variations to provide uniform implant to bone contact on both medial and lateral tibial condyles. It is critical to maintain anteroposterior divergence of the sub-components. Hence, the partially constrained interface between the sub-components is designed to constrain relative angulation generally in a transverse plane, axial translation and orthogonal translation generally in an anteroposterior direction. The remaining DOF, which are axial rotation, angulation generally in a sagittal plane and orthogonal translation generally in a superior-inferior direction, are unconstrained.

Figure 14:
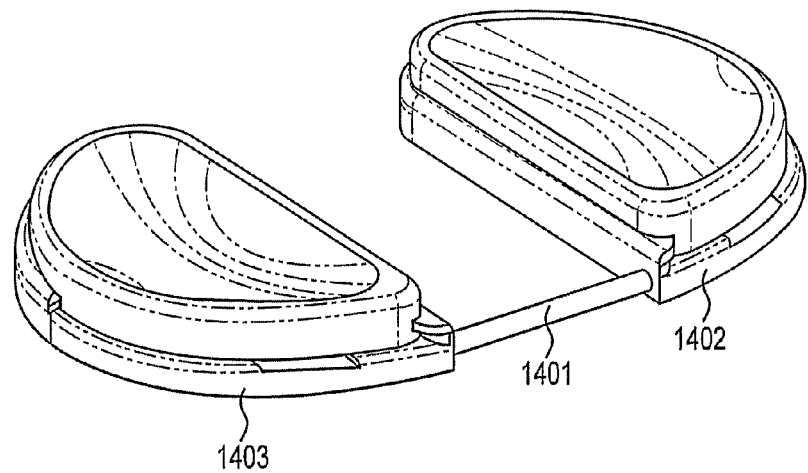
FIG. 14 is a plane view of a tibial component with sub-components connected with a flexible element according to an embodiment of the present invention.
Figure 15:
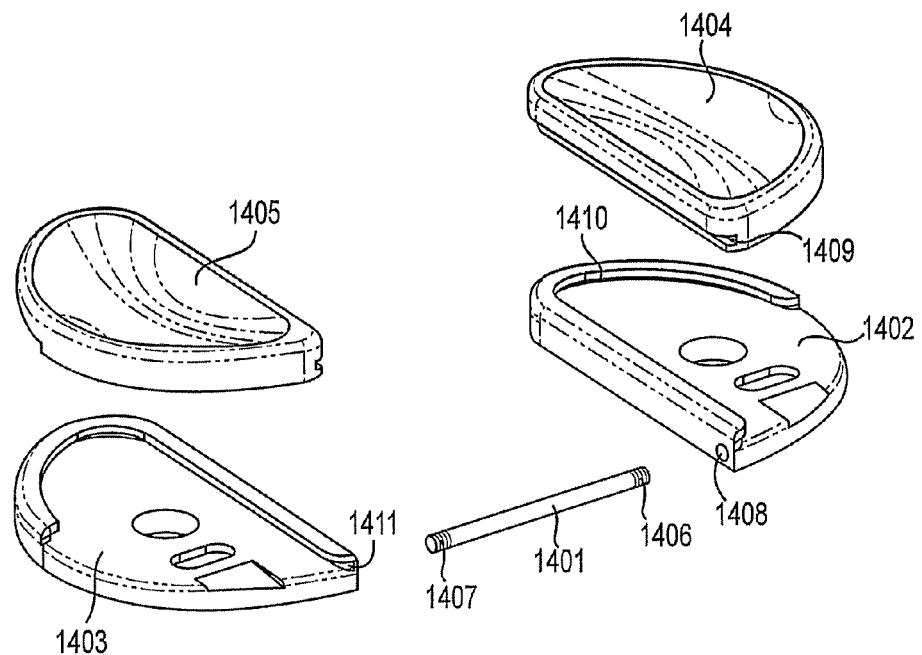
FIG. 15 is an exploded view of a tibial component with sub-components connected with a flexible element according to an embodiment of the present invention.

Referring to FIGS. 14 and 15, a tibial component is shown with a flexible component 1401 interconnecting the medial 1402 and lateral 1403 tibial baseplate sub-components. The flexible component may be may made from CoCr alloy or Titanium alloy. Alternatively, the wire (or cable) can be made from Nitinol or spring steel (NP35N) to enable flexing the assembled tibial component to place the component through a minimally invasive incision and allow the component to return to its original shape once in the joint cavity. The flexible component 1401 may has a circular cross section to allow equal resistance in bending under various bending moments.

Optionally, the flexible element may have a rectangular or square or oval cross section to stiffen bending resistance in select planes. A shown in FIG. 15, an exploded view of FIG. 14, the flexible component 1401 is attached to the tibial baseplate subcomponents 1402 and 1403 by threads 1407 and 1406 at both ends of the flexible component 1401 which are threaded into receiving holes 1411 (not shown) and 1408, respectively. Flexible component threaded section 1407 may be a right hand thread and the other end 1406 threaded with a left hand thread. The corresponding receiving holes are threaded to match. This allows threading the flexible element 1401 into the baseplate sub-components 1402 and 1403 at the same time. lateral tibial sub-components.

Figure 16:
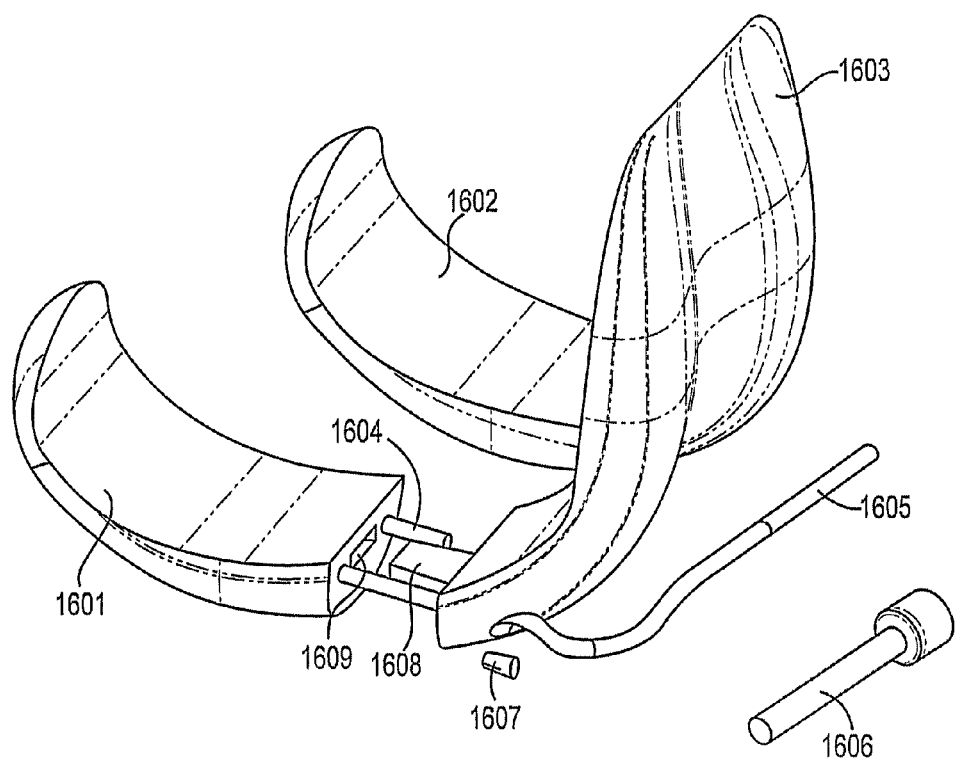
FIG. 16 is an orthogonal view of a femoral component with a condylar sub-component guided and attached with a tether according to an embodiment of the present invention.

Referring to FIG. 16, the femoral component is divided into three sub-components. The medial condylar 1601, lateral condylar 1602 and trochlear flange 1603. The sub-components are assembled by a rectangular tapered boss 1608 extending from the trochlear subcomponent 1603 and engaging receiving feature 1609 configured to snuggle receive boss 1608. A tether 1605 is used to guide and assemble the sub-components. Collet 1607 is used to secure the tether 1608 in the trochlear sub-component 1603. Insertion instrument 1606 is passed over the tether and pushes against the collet 1607 while the surgeon pulls on the tether 1605 to secure the sub-components together.

Figure 17:
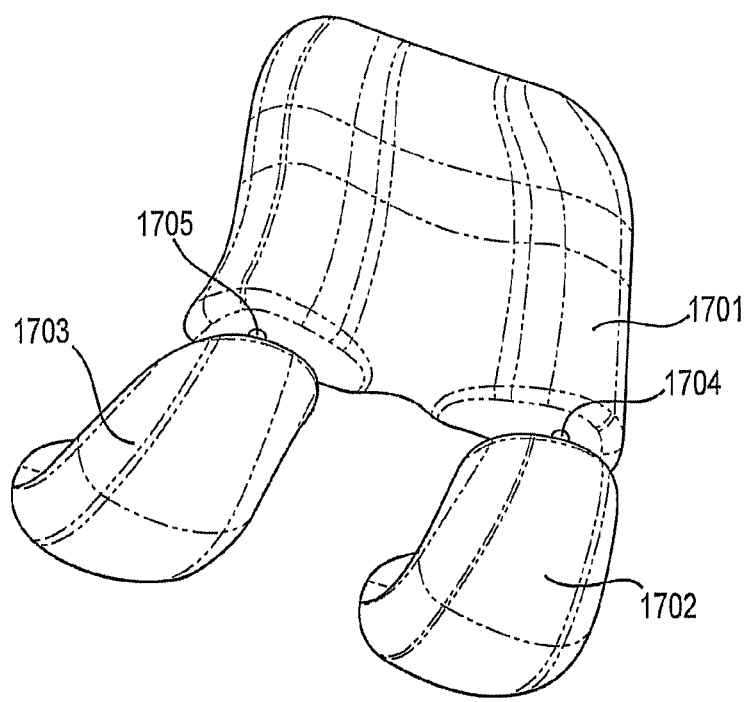
FIG. 17 is an orthogonal view of a femoral component with two sub-components connected with a flexible elements according to an embodiment of the present invention.
Figure 18:
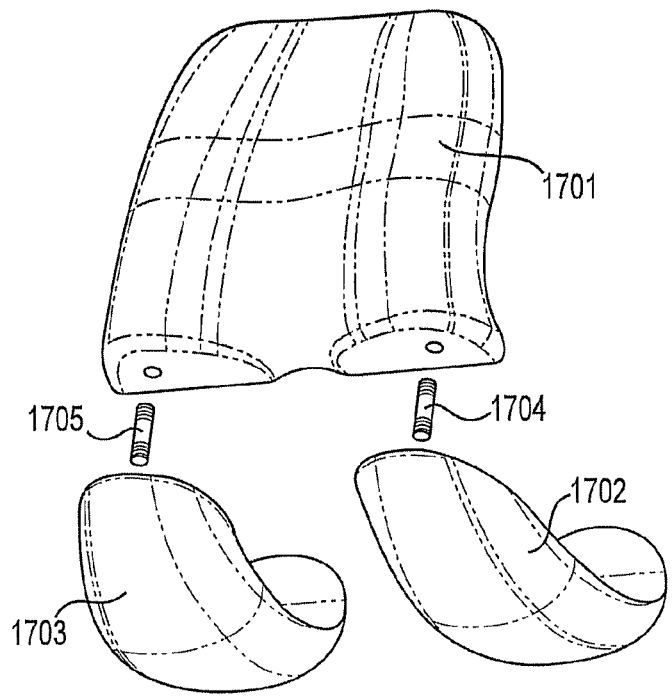
FIG. 18 is an exploded view of FIG. 17 according to an embodiment of the present invention.

As shown in FIGS. 17 and 18, a femoral component shown with three sub-components. Trochlear 1701, lateral condyle 1702 and medial condyle 1703 sub-components. The sub-components are held together with flexible components 1704 and 1705 that are threaded into each sub-component. Optionally, the flexible components 1704 and 1705 can be pressed into place, or other suitable fastening means. The sub-components may be assembled outside the joint cavity. Optionally, the sub-components are assembled within the confines of the joint cavity.

Figure 19:
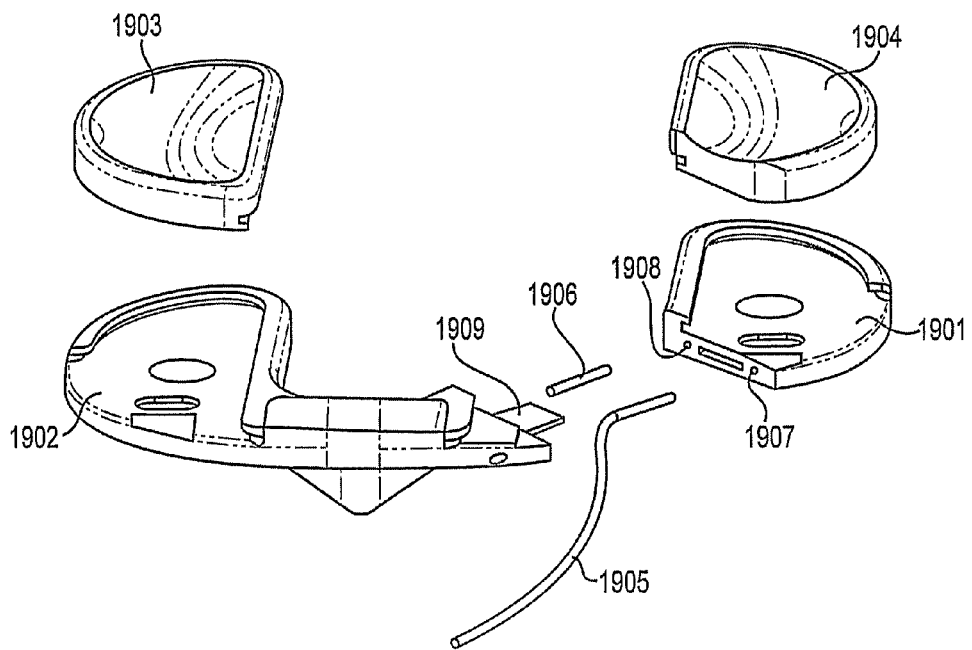
FIG. 19 is an exploded view of a tibial component with a two piece baseplate attached with a tether according to an embodiment of the present invention.

Similar to the femoral component shown in FIG. 18, a tibial component is shown in FIG. 19. The medial baseplate sub-component 1901 is assembled to the lateral sub-component 1902 by tether 1905 and aligned and secured by guide pin 1906 and boss 1909.

Figure 21:
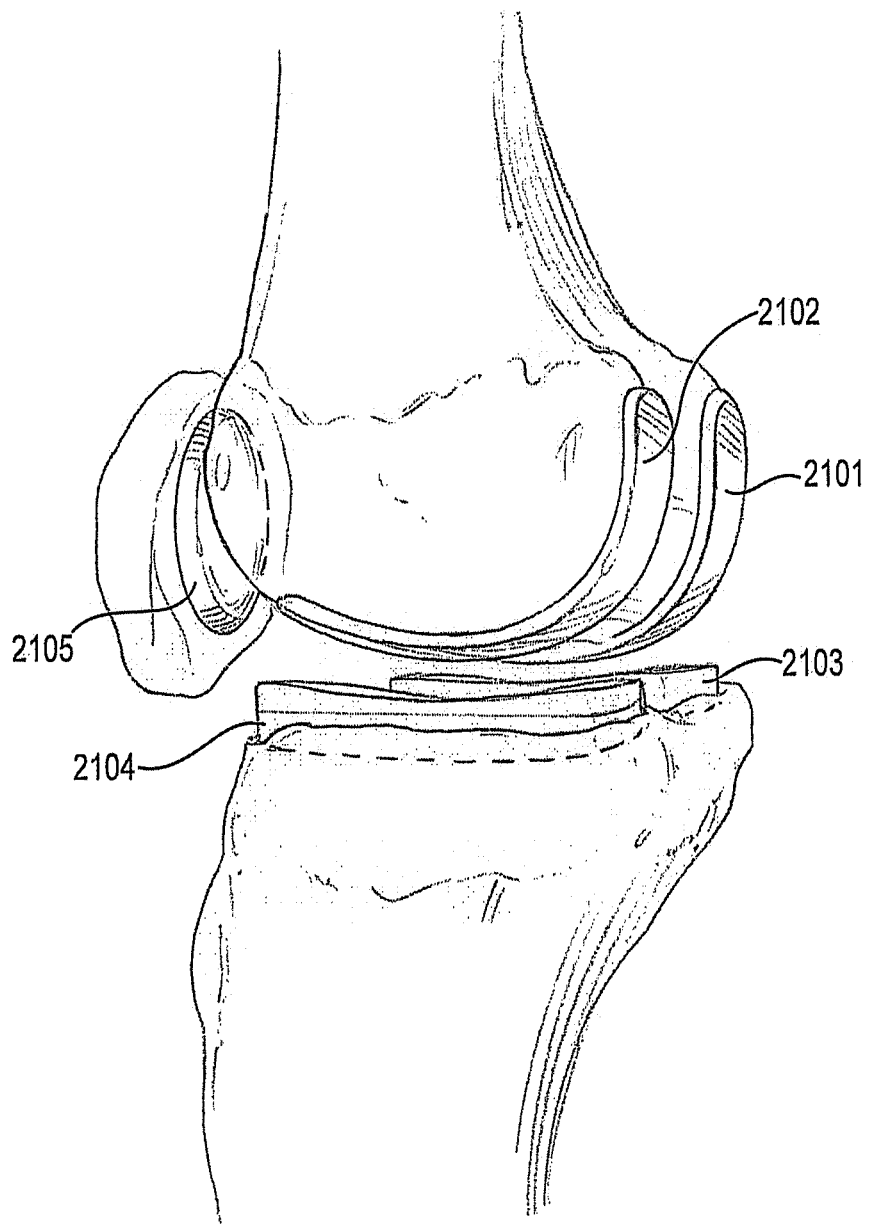
FIG. 21 illustrates femoral, tibial and patellar implants according to an embodiment of the present invention.
Figure 22:
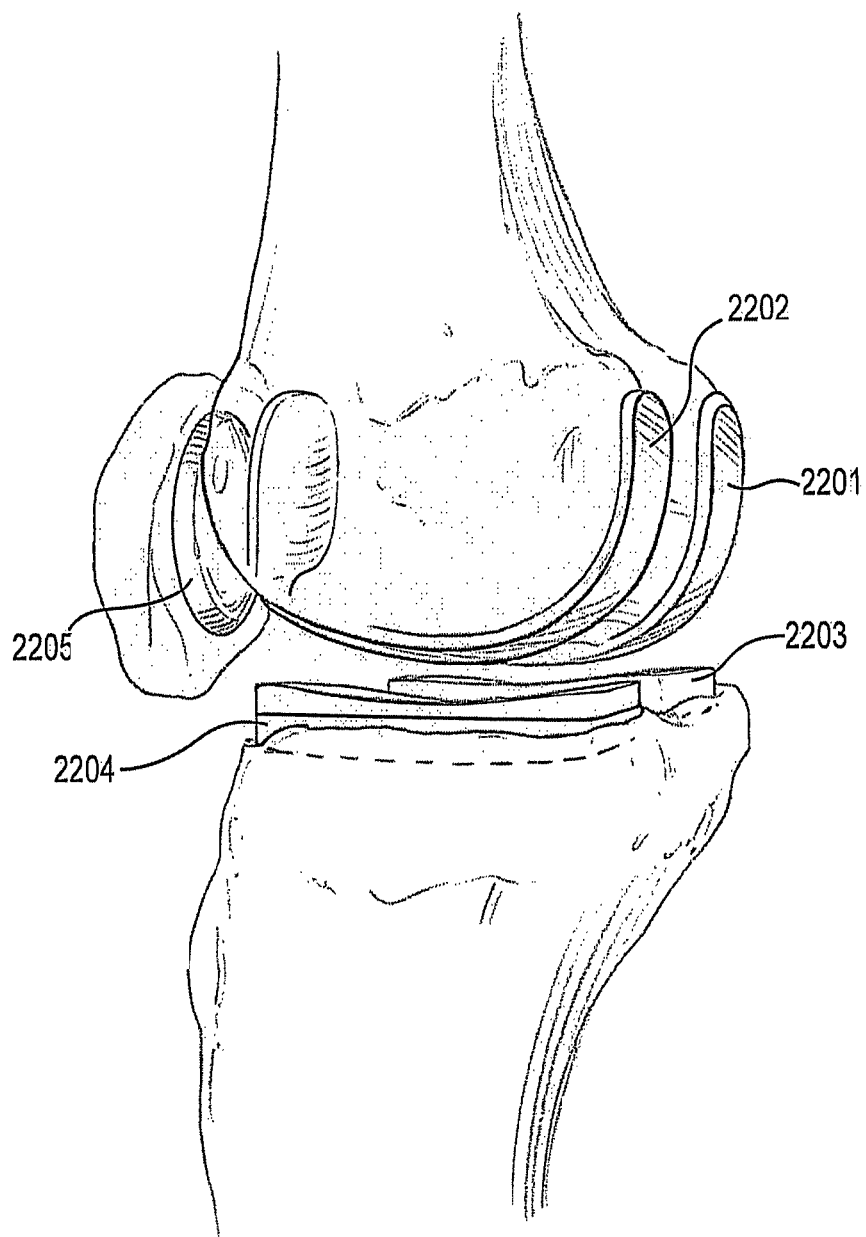
FIG. 22 illustrates femoral, tibial and patellar implants according to another embodiment of the present invention.

FIGS. 21 and 22 illustrate total knee arthroplasty components per the invention. In FIG. 21, the femoral condyles are resurfaced with condylar sub-components medially 2101 and laterally 2102, the tibial articular surfaces are resurfaced with tibial sub-components medially 2103 and laterally 2104. The patella is resurfaced with patellar component 2105. The femoral trochlea is not resurfaced. In FIG. 22, the femoral condyles are resurfaced with condylar sub-components medially 2201. The lateral condylar sub-component 2202 and trochlear component are integral, the tibial articular surfaces are resurfaced with tibial subcomponents medially 2203 and laterally 2204. The patella is resurfaced with patellar component 2205.

Additional components or steps as known to those skilled in the art may be performed within the scope of the invention. Further, one or more of the listed steps or components need not be performed in a procedure within the scope of the present invention. While a preferred embodiment of the present invention has been described, it should be understood that various changes, adaptations and modifications may be made therein without departing from the spirit of the invention and the scope of the appended claims.

What is claimed:

1. An apparatus comprising:
    a first bone implant including a plurality of sub-components for mimicking and replacing the bearing surfaces of a first bone, each of said plurality of subcomponents having an inner surface adapted to be secured to the first bone, each of said plurality of sub-components including a tethering hole;
    first bone flexible tethering means having an attachment end and a receiving end, said attachment end adapted to be receivably coupled to the tethering hole of a first of said plurality of first bone sub-components and the receiving end adapted to be receivably coupled to a second of said plurality of first bone sub-components wherein said tethering means are adapted to lock the second and subsequent of said plurality of first bone sub-components to the first of said plurality of first bone sub-components or to a second bone implant.

2. The apparatus of claim 1 wherein the attachment end of said tethering means is adapted to be receivably coupled to said tethering hole after said at least one of said plurality of first bone sub-components has been secured to the first bone.

3. The apparatus of claim 1 wherein said attachment end of said tethering means is adapted to be receivably coupled to said tethering hole outside of a joint cavity.

4. The apparatus of claim 2 wherein each remaining first bone subcomponent is adapted to be receivably coupled to the receiving end of said tethering means in succession and passed into the joint cavity.

5. The apparatus of claim 3 wherein each remaining first bone subcomponent is adapted to be received onto the receiving end of said tethering means in succession and engaged, aligned and/or oriented to each other outside of the joint cavity.

6. The apparatus of claim 1 wherein the sub-components of the first bone implant are structured to be engaged, aligned and/or oriented to each other within the confines of the joint cavity by said tethering means.

7. The apparatus of claim 1 further comprising a second bone implant including a plurality of second bone sub-components for mimicking and replacing the bearing surfaces of a second bone that articulates in a predetermined manner with the first bone, at least one of said plurality of said second bone sub-components including a tethering hole; and second bone flexible tethering means having an attachment end and a receiving end, the attachment end operably coupled to said tethering hole.

8. The apparatus of claim 7 wherein each of the plurality of second bone sub-components are structured to be receivably coupled to the receiving end of said tethering means in succession and passed into the joint cavity.

9. The apparatus of claim 8 wherein the plurality of second bone sub-components are structured to be engaged, aligned and/or oriented to each other within the confines of the joint cavity by said tethering means.

10. The apparatus of claim 7 wherein the first bone and second bone implants are selected from the group consisting of an ankle implant, a shoulder implant, a knee implant, a hip implant, a spinal implant, and a finger implant.

11. The apparatus of claim 7 wherein said first bone implant comprises a femoral implant and said second bone implant comprises a tibial bearing insert and a tibial baseplate wherein the attachment end of the tethering means is structured to be receivably coupled to the tethering hole of at least one of said plurality of femoral sub-components, said tibial baseplate sub-components, or both.

12. The apparatus of claim 11 wherein said tethering means is structured to be coupled to the tethering hole of said at least one of said plurality of femoral sub-components after said at least one of said plurality of femoral sub-components is secured to the femur.

13. The apparatus of claim 11 wherein said tethering means is structured to be receivably coupled to the tethering hole of at least one of said plurality of said femoral sub-components outside of a joint cavity.

14. The apparatus of claim 13 wherein each remaining femoral sub-component is structured to be receivably coupled to the receiving end of said tethering means in succession and engaged, aligned and/or oriented to each other outside the joint cavity.

15. The apparatus of claim 11 wherein said tethering means is structured to be receivably coupled to the tethering hole of at least one of said plurality of tibial baseplate sub-components outside of a joint cavity.

16. The apparatus of claim 15 wherein each remaining tibial baseplate sub-component is structured to be receivably coupled to the receiving end of said tethering means in succession and engaged, aligned and/or oriented to each other outside the joint cavity.

17. The apparatus of claim 11 wherein each femoral and tibial baseplate sub-component is structured to be joined, aligned and/or oriented one to the other within the confines of the joint cavity by said tethering means.

18. The apparatus of claim 7 further comprising second bone tethering means having an attachment end and a receiving end, said attachment end adapted to be receivably coupled to the tethering hole of said at least one of said plurality of second bone sub-components.

19. The apparatus of claim 1 wherein said tethering means are structured to be coupled to each first bone sub-component and remain in a joint cavity after alignment of said first bone subcomponents.

20. The apparatus of claim 11 wherein the plurality of bearing-surface femoral sub-components are selected from the group consisting of trochlear, medial femoral condyle and lateral femoral condyle sub-components.

21. The apparatus of claim 11 wherein the attachment end of said tethering means is structured to be removably coupled to said tethering hole of at least one of said plurality of femoral sub-components or at least one of said plurality of tibial baseplate sub-components, or both.

22. The apparatus of claim 11 wherein the attachment end of said tethering means is structured to be fixedly coupled to said tethering hole of at least one of said plurality of femoral sub-components or at least one of said plurality of tibial baseplate sub-components, or both.

23. The apparatus of claim 18 wherein the attachment end and the receiving end of said first bone and/or said second bone tethering means are structured to be removably coupled to said first bone and/or said second bone subcomponents and removed from a joint cavity after engagement, alignment and/or orientation of said first bone sub-components and said second bone sub-components.

24. The apparatus of claim 18 wherein the attachment end and the receiving end of said first bone and/or said second bone tethering means are structured to be fixedly coupled to the tethering hole of at least one of said first bone and/or said second bone subcomponents and remain in a joint cavity after engagement, alignment and/or orientation of said first bone sub-components and said second bone sub-components.

25. The apparatus of claim 1 wherein said flexible tethering means comprise wires, cables, lines, filaments, sutures, braids, tape, threads, strands, or cords.

26. The apparatus of claim 1 wherein a first of said plurality of sub-components is structured to be receivably coupled to said flexible tethering means and adapted to be secured to the first bone, and further wherein each remaining sub-component is structured to be receivably coupled to the receiving end of said tethering means in succession and passed into the joint cavity.

27. The apparatus of claim 1 wherein said first bone tethering means comprise a plurality of tethering means.

28. The apparatus of claim 5 or 6 further comprising a tensioner for applying a compressive force to the sub-components to engage said sub-components one to the other.

29. An apparatus comprising:
a first bone implant including a plurality of first bone sub-components for mimicking and replacing the bearing surfaces of the first bone, each of said plurality of first bone sub-components having an inner surface adapted to be secured to the first bone, wherein each of said plurality of first bone sub-components includes a threaded tethering hole; and
first bone flexible tethering means having an attachment end and a receiving end, said attachment end structured adapted to be coupled to the first bone and said receiving end threadably received by each of said threaded tethering holes adapted to secure each of said plurality of first bone sub-components to said first bone, to a first of said plurality of first bone sub-components, to a second bone or to a second bone implant.

30. The apparatus of claim 29 further comprising a second bone implant including a plurality of second bone sub-components for mimicking and replacing the bearing surfaces of a second bone that articulates in a predetermined manner with the first bone, at least one of said plurality of second bone sub-components having a threaded tethering hole; and
second bone flexible tethering means having an attachment end and a receiving end, said attachment end structured to be coupled to the second bone and said receiving end threadably received by said tethering hole to secure said at least one of said plurality of second bone sub-components to said second bone.

31. The apparatus of claim 29 wherein said flexible tethering means comprises wires, cables, lines, filaments, sutures, braids, tapes, threads, strands, or cords.

32. The apparatus of claim 29 wherein a first of said plurality of sub-components is structured to be receivably coupled to said flexible tethering means and adapted to be secured to the first bone, and further wherein each remaining sub-component is structured to be receivably coupled to the receiving end of said tethering means in succession and passed into the joint cavity.

33. An apparatus for partially replacing the femoral surfaces of a knee joint, the apparatus comprising:
a femoral implant including a plurality of bearing-surface sub-components, each of said plurality of bearing-surface sub-components having an inner surface adapted to be secured to a femur, each of said plurality of femoral sub-components including a tethering hole; and
flexible tethering means having an attachment end and a receiving end, said attachment end structured to be receivably coupled to the tethering hole of a first of said plurality of femoral sub-components outside of a joint cavity,
wherein said first of said plurality of femoral sub-components is structured to be receivably coupled to said flexible tethering means and adapted to be secured to the first bone, and further wherein subsequent femoral sub-components are structured to be receivably coupled to the receiving end of said tethering means in succession and passed into the joint cavity and further wherein said tethering means are adapted to lock each subsequent femoral sub-component to the first of said plurality of femoral sub-components or to a second bone implant.

34. The apparatus of claim 33 wherein the femoral sub-components are aligned, engaged and/or oriented to each other within the confines of the joint cavity by said flexible tethering means.

* * * * *